(12) United States Patent
Waldron et al.

(10) Patent No.: US 9,211,060 B2
(45) Date of Patent: Dec. 15, 2015

(54) VISUALIZATION DEVICE AND HOLDER FOR USE WITH A TRACHEAL TUBE

(75) Inventors: Paul Waldron, Galway (IE); Seamus Maguire, Athlone (IE)

(73) Assignee: Covidien LP, Mansfield, MA (US)

( * ) Notice: Subject to any disclaimer, the term of this patent is extended or adjusted under 35 U.S.C. 154(b) by 476 days.

(21) Appl. No.: 13/080,226

(22) Filed: Apr. 5, 2011

(65) Prior Publication Data
US 2012/0259173 A1    Oct. 11, 2012

(51) Int. Cl.
   *A61B 1/04*    (2006.01)
   *A61B 1/267*   (2006.01)
   *A61B 1/00*    (2006.01)
   *A61B 1/015*   (2006.01)
   *A61M 16/04*   (2006.01)

(52) U.S. Cl.
   CPC ............. *A61B 1/267* (2013.01); *A61B 1/00073* (2013.01); *A61B 1/00082* (2013.01); *A61B 1/015* (2013.01); *A61B 1/2676* (2013.01); *A61M 16/0434* (2013.01); *A61M 16/0479* (2014.02); *A61M 16/0484* (2014.02); *A61M 16/0488* (2013.01); *A61M 2205/3306* (2013.01); *A61M 2205/502* (2013.01)

(58) Field of Classification Search
   CPC .......... A61B 1/00101; A61B 1/00103; A61B 1/00105; A61B 1/00108; A61B 1/00147; A61B 1/05; A61B 1/051
   USPC .................................................. 600/120, 194
   See application file for complete search history.

(56) References Cited

U.S. PATENT DOCUMENTS

| | | | |
|---|---|---|---|
| 4,233,984 A | 11/1980 | Walling |
| 4,685,457 A | 8/1987 | Donenfeld |
| 4,846,153 A | 7/1989 | Berci |
| 4,949,716 A | 8/1990 | Chenoweth |
| 4,982,729 A | 1/1991 | Wu |
| 5,016,614 A | 5/1991 | MacAllister |
| 5,038,766 A | 8/1991 | Parker |
| 5,174,283 A | 12/1992 | Parker |

(Continued)

FOREIGN PATENT DOCUMENTS

| WO | WO2008103448 | 8/2008 |
|---|---|---|
| WO | WO2010091440 | 8/2010 |

OTHER PUBLICATIONS

Salem, MR, "Verification of Endotracheal Tube Position", Anesthesiology Clinics of North America, vol. 19(4); pp. 831-839 (Dec. 1, 2001).

(Continued)

*Primary Examiner* — Matthew J Kasztejna
(74) *Attorney, Agent, or Firm* — Fletcher Yoder PC (57) ABSTRACT

The present disclosure describes systems and methods that utilize a tracheal tube with an integral visualization device, such as a camera. The tracheal tube system may include a camera apparatus or other visualization device that is associated with a lumen formed in the wall of the tube. In addition, the camera apparatus may be positioned within a holder associated with a distal end of the tracheal tube that functions to hold and position the optical components of the camera relative to the tube and provides an acceptable profile for comfortable intubation. Further, the camera apparatus and its associated holder may include additional components, such as integral light sources and flushing or cleaning devices to remove any buildup from the camera or optical components.

20 Claims, 8 Drawing Sheets

(56) References Cited

U.S. PATENT DOCUMENTS

| | | | |
|---|---|---|---|
| 5,203,320 | A | 4/1993 | Augustine |
| 5,259,377 | A | 11/1993 | Schroeder |
| 5,285,778 | A | 2/1994 | Mackin |
| 5,287,848 | A * | 2/1994 | Cubb et al. ............... 128/200.26 |
| 5,329,940 | A | 7/1994 | Adair |
| 5,339,805 | A | 8/1994 | Parker |
| 5,363,838 | A | 11/1994 | George |
| 5,392,766 | A * | 2/1995 | Masterson et al. ............ 600/157 |
| 5,400,771 | A * | 3/1995 | Pirak et al. .................... 600/109 |
| 5,536,236 | A * | 7/1996 | Yabe et al. .................... 600/129 |
| 5,607,386 | A | 3/1997 | Flam |
| 5,636,625 | A | 6/1997 | Miyagi et al. |
| 5,645,519 | A * | 7/1997 | Lee et al. ...................... 600/194 |
| 5,665,052 | A * | 9/1997 | Bullard ......................... 600/194 |
| 5,694,929 | A | 12/1997 | Christopher |
| 5,735,792 | A * | 4/1998 | Vanden Hoek et al. ........ 600/138 |
| 5,842,973 | A * | 12/1998 | Bullard ......................... 600/194 |
| 5,845,634 | A * | 12/1998 | Parker ...................... 128/200.26 |
| 5,913,816 | A * | 6/1999 | Sanders et al. ................ 600/120 |
| 5,921,917 | A | 7/1999 | Barthel et al. |
| 5,964,217 | A | 10/1999 | Christopher |
| 6,142,144 | A | 11/2000 | Pacey |
| 6,189,533 | B1 | 2/2001 | Simon et al. |
| 6,196,225 | B1 | 3/2001 | Allegeyer |
| 6,315,739 | B1 | 11/2001 | Merilainen et al. |
| 6,447,445 | B1 * | 9/2002 | Hirano .......................... 600/129 |
| 6,450,164 | B1 | 9/2002 | Banner et al. |
| 6,520,183 | B2 | 2/2003 | Amar |
| 6,543,446 | B1 | 4/2003 | Christopher |
| 6,568,388 | B2 | 5/2003 | Christopher |
| 6,629,924 | B2 | 10/2003 | Aydelotte |
| 6,631,713 | B1 | 10/2003 | Christopher |
| 6,672,305 | B2 | 1/2004 | Parker |
| 6,820,618 | B2 | 11/2004 | Banner et al. |
| 6,849,042 | B2 | 2/2005 | Christopher |
| 6,860,264 | B2 | 3/2005 | Christopher |
| 6,929,600 | B2 | 8/2005 | Hill |
| 7,051,736 | B2 | 5/2006 | Banner et al. |
| 7,052,456 | B2 | 5/2006 | Simon |
| 7,128,071 | B2 * | 10/2006 | Brain ....................... 128/207.15 |
| 7,942,813 | B2 * | 5/2011 | Mackin ......................... 600/120 |
| 2005/0039754 | A1 * | 2/2005 | Simon ...................... 128/207.14 |
| 2006/0025650 | A1 | 2/2006 | Gavriely |
| 2006/0122460 | A1 | 6/2006 | Kamali |
| 2007/0137651 | A1 | 6/2007 | Glassenberg et al. |
| 2007/0175482 | A1 * | 8/2007 | Kimmel et al. .......... 128/207.14 |
| 2008/0039715 | A1 | 2/2008 | Wilson et al. |
| 2010/0030057 | A1 | 2/2010 | Gavriely |
| 2010/0174144 | A1 * | 7/2010 | Hsu et al. ...................... 600/122 |
| 2012/0024292 | A1 | 2/2012 | Sandmore et al. |
| 2012/0172664 | A1 | 7/2012 | Hayman et al. |

OTHER PUBLICATIONS

Kristensen, MS, "The Parker Flex-Tip Tube versus a Standard Tube for Fiberoptic Orotracheal Intubation", Anesthesiology, vol. 98, No. 2, Feb. 2003.

Kohase, H. et al., "Endotracheal Intubation Device with a Charge Couple Device Camera", Anesth, Analg. 2003; 96:432-4.

Makino, H. et al., "The Effects of Traceal Tube Tip Design and Tube Thickness on Laryngeal Pass Ability During Oral Tube Exchange with an Introducer", Anesth Analg 2003; 97:285-8.

Sehata, H. et al., "Tracheal intubation using a new CCD camera-equipped device: a report of two cases with a difficult intubation", Acta Anaesthesiologica Scandinavica, vol. 49, No. 8, Sep. 2005, pp. 1218-1220(3).

Kaplan, MB et al., "Seeing is believing: the importance of video laryngoscopy in teaching and in managing the difficult airway", Surg. Endosc. 2006 20:S479-83. Epub Mar. 16, 2006.

Amdt Endobronchial Blocker, Cook Medical, http://www.cookmedical.com/cc/familyListingAction.do?family=Endobronchial+Blockers.

Cohen Endobronchial Blocker, Cook Medical, http://www.cookmedical.com/cc/familyListingAction.do?family=Endobronchial+Blockers.

Portex, Endobronchial Double Lumen, Smiths-Medical, http://www.smiths-medical.com/catalog/endotracheal-tubes.

Tuteja, A., et al., "Robust omniphobic surfaces", PNAS. Nov. 25, 2008, vol. 105, No. 47.

Respiratory Care—http://www.smiths-medical.com/markets/repiratory-care/ (Apr. 1, 2010).

PCT/US2011/063492 International Search Report and Written Opinion mailed Apr. 2, 2012.

* cited by examiner

VISUALIZATION DEVICE AND HOLDER FOR USE WITH A TRACHEAL TUBE

BACKGROUND

The present disclosure relates generally to medical devices and, more particularly, to tracheal tubes that may accommodate an integral visualization device, such as a camera.

This section is intended to introduce the reader to various aspects of art that may be related to various aspects of the present disclosure, which are described and/or claimed below. This discussion is believed to be helpful in providing the reader with background information to facilitate a better understanding of the various aspects of the present disclosure. Accordingly, it should be understood that these statements are to be read in this light, and not as admissions of prior art.

In the course of treating a patient, a tracheal tube (e.g., endotracheal, endobronchial, nasotracheal, or transtracheal device) may be used to control the flow of gases into the trachea of a patient. Often, a seal between the outside of the tube and the interior wall of the tracheal lumen is required, allowing for generation of positive intrathoracic pressure distal to the seal and prevention of ingress of solid or liquid matter into the lungs from proximal to the seal.

For example, a patient may be intubated when an endotracheal tube is inserted through the patient's mouth and into the trachea. Often, such intubation procedures may be performed during medical emergencies or during critical care situations. As such, healthcare providers may balance a desire for speed of intubation with a desire for accurate placement of the tube within the trachea. However, proper placement of a tracheal tube may be complex. In certain situations, placement may be aided with visualization of the trachea performed during laryngoscopy. During an intubation procedure, a practitioner may employ a lighted laryngoscope during introduction of the endotracheal tube. However, often the visualization of the trachea is poor because of patient secretions that may obscure the laryngoscope. In addition, such visualization during introduction of the tube may not account for ongoing changes in the tube's position within the trachea that may occur when a patient coughs, which may dislodge a tube from its desired location, or when a patient is jostled or moved within a care setting, which may change the position or angle of the tube within the trachea.

BRIEF DESCRIPTION OF THE DRAWINGS

Advantages of the disclosed techniques may become apparent upon reading the following detailed description and upon reference to the drawings in which.

DETAILED DESCRIPTION OF SPECIFIC EMBODIMENTS

One or more specific embodiments of the present techniques will be described below. In an effort to provide a concise description of these embodiments, not all features of an actual implementation are described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

As described in detail below, embodiments of a tracheal tube having an integral visualization apparatus, e.g., a camera, are provided herein. The tracheal tubes provided herein include built-in visualization devices that facilitate proper placement of the tube through the vocal cords into the trachea and intermittent or continuous corroboration of positioning over the course of intubation. In addition, for embodiments in which visualization devices may be incorporated into endobronchial tubes, the visualization devices may facilitate subsequent proper placement and corroboration of appropriate positioning within the appropriate mainstem bronchus. The visualization devices as provided may facilitate intermittent or continuous evaluation of a patient's medical condition via assessment of changes within the trachea or airway tissue (e.g. hemorhage, accumulation of secretions, lung volume expansion, etc).

The integral visualization devices may be positioned at least in part within lumens running alongside the main ventilation lumen of the tube. For example, the visualization devices may be positioned within a tube's cuff inflation line or evacuation line. In particular embodiments, the visualization devices may be associated with a distal, unused portion of an evacuation line. Because suction lumens are typically formed in a tracheal tube wall through an extrusion process, the suction lumens run alongside the entire length of the tracheal tube. However, only the portion of the suction lumen that is generally above the cuff is used for suctioning secretions. As provided herein, the distal portion of the suction lumen may be used to accommodate a visualization device. In this manner, in particular embodiments, existing extrusion processes for forming tracheal tubes and associated secondary lumens may be used in conjunction with the visualization devices as provided.

Visualization device that are positioned within lumens formed within the walls of the main ventilation lumen have minimal impact on the inner diameter of the main ventilation lumen. As a result, a tracheal tube may include visualization functionality with no significant change in resistance to gas flow through the tube lumens, no interruption or reduction of fresh gas ventilation. In additional, insertion of the tracheal tube or visualization of the tracheal tissue after intubation may be accomplished without a bronchoscope.

The tracheal tubes may further be used in conjunction with acceptable auxiliary airway devices such as (e.g. heat and humidity conservers, filters, mechanical ventilators, humidifiers, closed suction systems, scavengers, capnometers, oxygen analyzers, mass spectrometers, PEEP/CPAP devices, etc). Furthermore, although the embodiments of the present disclosure illustrated and described herein are discussed in the context of tracheal tubes such as endotracheal tubes, it should be noted that presently contemplated embodiments may include a visualization device associated with any of a variety of suitable airway devices. For example, a visualization device as provided herein may be associated with a single-lumen tube, a tracheostomy tube, a Broncho-Cath™ tube, a specialty tube, or any other airway device with a main ventilation lumen. Indeed, any device with a ventilation lumen designed for use in an airway of a patient may include a visualization device (e.g., a camera disposed within a holding device). Furthermore, as used herein, the term "tracheal tube" may include an endotracheal tube, a tracheostomy tube, a Broncho-Cath™ tube, a bronchoblocking tube, a specialty tube, or any other suitable airway device.

Figure 1:
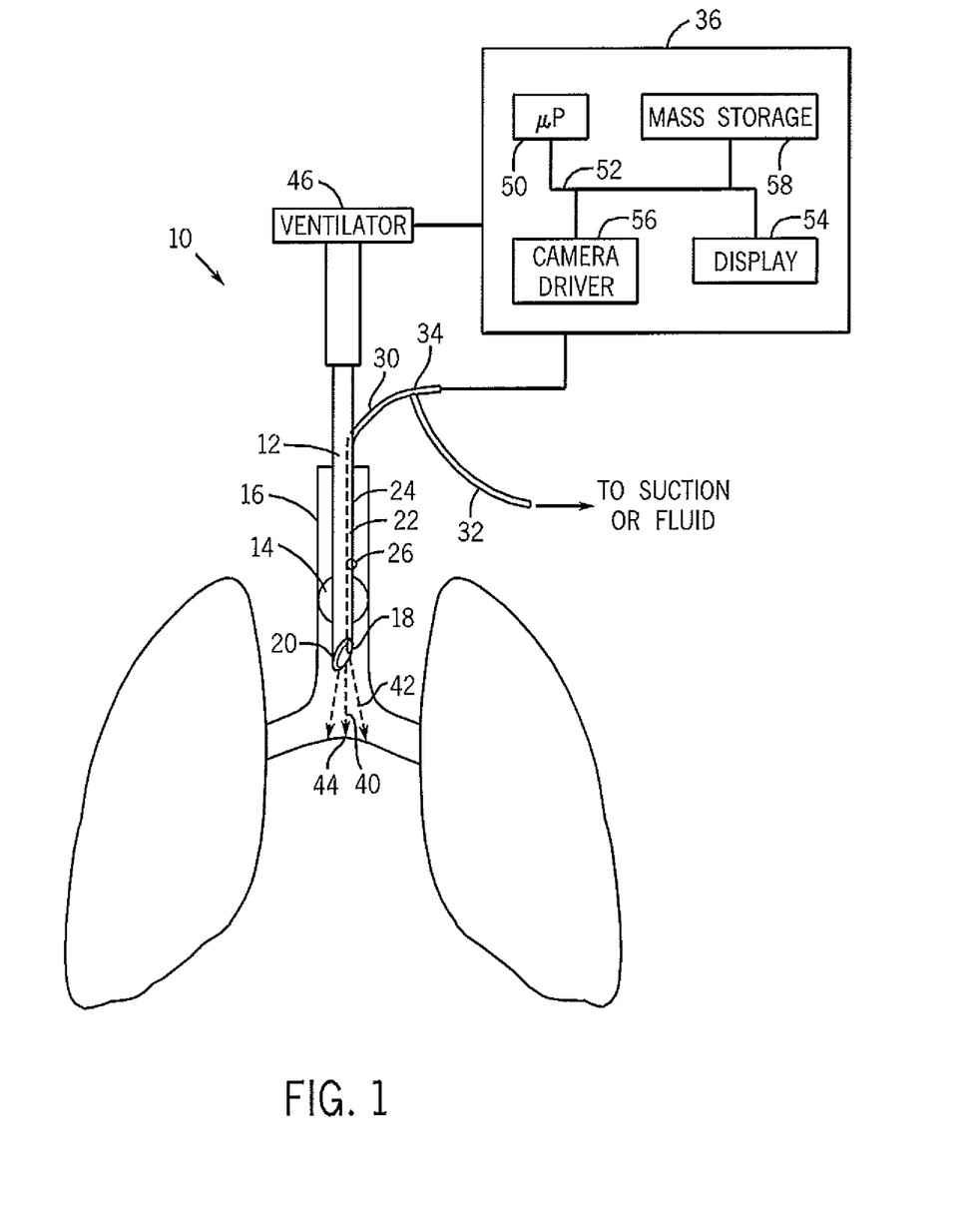
FIG. 1 is a view of a system with a tracheal tube including a visualization device in accordance with aspects of the present disclosure.

FIG. 1 shows an exemplary tracheal tube system 10 that includes a tracheal tube 12, shown here as endotracheal tube, with an inflatable balloon cuff 14 that may be inflated to form a seal against tracheal walls 16. The tracheal tube 12 may also include a visualization device 18 that is associated with a distal end 20 of the tube 12. In the depicted embodiment, the visualization device 18 is positioned within a lumen 22 formed in an exterior wall 24 of the tube 12. The lumen 22 may also serve as a suction lumen. In such embodiments, the lumen 22 may include a notch 26 or opening positioned above the cuff 14 to facilitate the removal of secretions that have accumulated above the cuff 14. The lumen 22 may also feature a proximal connecting portion 30 that splits into connecting portion 32 for connection to a suction source and connecting portion 34 for connection of the visualization device 18 to a visualization monitor 36. To that end, suitable electrical connectors to the visualization device, including any fiber optic cables and light sources, may be positioned in the lumen 22.

The visualization device 18 may be oriented in any suitable direction, depending on the desired field of view. In the depicted embodiment, the visualization device is oriented along an axis corresponding with arrow 40 so that the field of view 42 is generally pointed towards a carina 44. That is, the center axis 40 of the field of view 42 lines up with a desired visualization target. In other embodiments, the desired visualization target may include a left or right bronchus.

The system 10 may also include devices that facilitate positive pressure ventilation of a patient, such as a ventilator 46, which may include any ventilator, such as those available from Nellcor Puritan Bennett LLC. As noted, the system may also include a visualization monitor 36 that may be configured to implement embodiments of the present disclosure. The monitor 36 may be a stand-alone device or may be coupled to another patient monitor or to the ventilator 46. The monitor 36 may include a microprocessor 50 coupled to an internal bus 52 and a display 54. The monitor 36 may include certain elements for controlling the visualization device, such as s camera driver 56 that may include drivers for one or more light sources. In an embodiment, the monitor 36 may be configured to receive signals from the visualization device 18 and store the signals in a mass storage device 58, such as a RAM, ROM, optical storage device, flash memory device, hardware storage device, magnetic storage device, or any other suitable device permitting memory storage. The signals may be accessed and operated according to instructions for a microprocessor 32. In certain embodiments, the signals may be related to visualization of the patient anatomy around the tracheal tube 12 and may be processed by the monitor 36 to indicate, for example, whether the tracheal tube 12 is properly placed. The monitor 36 may be configured to provide an indication about the placement of the tracheal tube 12 within the patient's trachea, such as an audio alarm, visual alarm or a display message if the tracheal tube 12 is too far or too close to certain anatomical structures, such as the carina 44.

Figure 2:
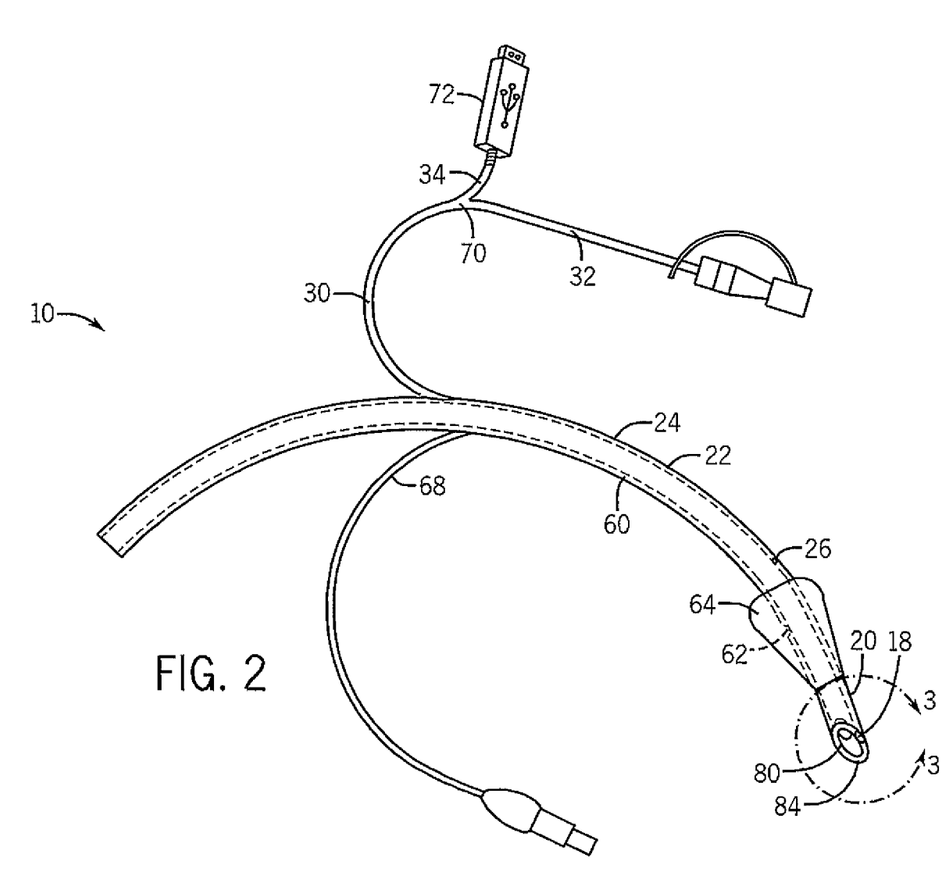
FIG. 2 is a perspective view of a tracheal tube that may be used with the system of FIG. 1.

FIG. 2 is a perspective view of an exemplary tracheal tube 12 including a visualization device 18. As provided, the visualization device 18 may be positioned in a lumen formed proximate to or within an exterior wall 24 of the tracheal tube 12. The lumen may be a dedicated lumen or, in particular embodiments, may be a lumen that has additional functionality, such as suction or cuff inflation. As shown, the tube 12 includes cuff 14 that may be inflated via inflation lumen 60. The lumen 60 opens via a notch 62 through the exterior wall 24 into the interior space 64 of the cuff 14. The inflation lumen 60 is operatively connected to proximal inflation line 68, which may connect to a syringe or other inflation source. The tracheal tube 12 may also include suction lumen 22 for aspirating secretions that may form above the cuff 14 through opening 26. In one embodiment, the lumen 22 may also facilitate flushing or cleaning of the visualization device 18. For example, the lumen 22 may terminate in a distal coupler 69 that is sized and shaped to connect to a suction source or a fluid source (e.g., a saline reservoir, a syringe). The tube 12 may also include a cable coupled to the visualization device 18 that runs along or within the tube 12. The proximal connecting portion 30 may split via a Y-connector 70 into connecting portion 32 for connection to a suction source and connecting portion 34 that may include an electrical connector 72, such as a USB connector, which may be coupled to the cable.

The visualization device 18 may include a camera and a holder for affixing the camera to the tracheal tube 12 at the distal end of the tube 12. As shown, the visualization device 18 is positioned at the distal tip 84, opposite the Murphy eye 80. The camera may be any suitable camera, including a miniature camera, a fiber optic camera, a camera that includes a charge coupled device (CCD), or CMOS imaging sensor. In one embodiment, the visualization device 18 includes a CMOS image sensor and an associated light source, such as an LED. However, in other embodiments, the visualization device 18 may include other types of sensors or imaging devices, including ultrasound transceivers.

The tube 12 and the cuff 14 may be formed from materials having desirable mechanical properties (e.g., puncture resistance, pin hole resistance, tensile strength, and so forth) and desirable chemical properties (e.g., biocompatibility). Further, in one embodiment, the walls of the cuff 14 may be made of a polyurethane (e.g., Dow Pellethane® 2363-80A) having suitable mechanical and chemical properties. In other embodiments, the walls of the cuff 14 may be made of silicone or a suitable polyvinyl chloride (PVC). In certain embodiments, the cuff 14 may be generally sized and shaped as a high volume, low pressure cuff that may be designed to be inflated to pressures between about 15 cm $H_2O$ and 30 cm $H_2O$. In addition, to assist in proper placement of the tube 12, x-ray visible markings may be placed at any appropriate location.

In certain embodiments, the tube 12 may be extruded. Secondary lumens, such as lumens that accommodate the visualization device 18, may be formed along or in the exterior wall of the tube 12 during the extrusion process. In certain embodiments, tracheal tubes 12 may be provided in various sizes that are suited to different patients. The tube size may dictate the inner and outer diameter of the tube 12. This in turn may influence the size of associated secondary lumens, such as suction lumen 22 or cuff inflation lumen 60. In certain embodiments, the lumen with which the visualization device 18 is associated has an inner diameter of about 3 millimeters or less. Such lumens may be used in conjunction with appropriately sized camera components, such as fiber optic cables that are about 1 mm or less in diameter. For a camera arrangement with an emitting and detecting cable, both cables may be accommodated within a secondary lumen that is at least 2 mm in diameter. For tubes 12 that are smaller sizes, e.g., tubes that are 6 millimeters in inner diameter, or tubes 12 that have smaller secondary lumens, the components of the visualization device 18 may be selected to fit within the available space within the lumen. For example, fiber optic cables (e.g., an emitting and detecting cable) that are 0.75 mm in diameter or less may be used. In other embodiments, depending on the arrangement of the visualization device 18, the lumen may be larger or may have sections that are larger to accommodate certain components.

In one embodiment, the distal tip 84 is formed by cutting the distal end 20 of an extruded tube section at a slant. After the tube is cut, the distal end 84 may be shaped with a melt mold. In such embodiments, the distal end 20 of the appropriate lumen (e.g., a dedicated lumen for the visualization device 18 or the suction lumen 22) may be kept open during the melt mold process instead of being sealed. In one embodiment, the melt mold may include a protrusion sized and shaped to align with the lumen and prevent sealing during shaping of the distal tip 84. After the tube 12 is formed, the cuff 14 and the visualization device 18 may be applied to the tube 12. In one embodiment, the camera, leads, or cables associated with the visualization device 18 may be threaded into the appropriate lumen. The housing (e.g., a holder) and/or other associated optical components may then be coupled to the leads, and the visualization device 18 may be adhered or affixed to the tube 12.

Figure 3:
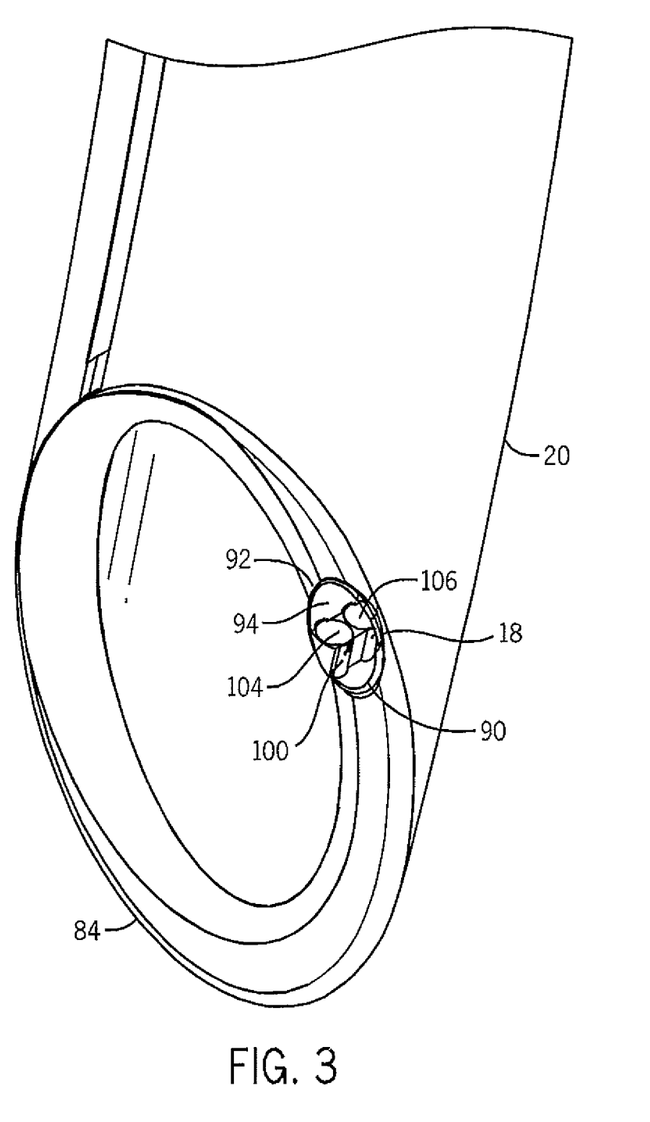
FIG. 3 is a detailed view of the distal tip and visualization device of the tracheal tube of FIG. 2.

FIG. 3 is a detail view of the distal end 20 of the tube 12. The visualization device 18 includes a holder 90 that facilitates alignment of a camera 91 with the tube 12. The holder includes an exterior portion 92 that is disposed on or outside the suction lumen 22 and is visible to an observer. As illustrated, the exterior portion 92 may include a surface 94 that generally conforms to the angle of the distal tip. In this manner, the visualization device 18 does not significantly protrude from the tube 12, which facilitates insertion of the tube 12. The exterior portion 92 may be formed as a flange or other shaped region that has a diameter that is larger than a diameter of the lumen into which the visualization device 18 has been inserted, which may prevent insertion of the visualization device into the lumen (e.g., lumen 22 in FIG. 2) beyond a particular depth to facilitate alignment of the camera 91 with the tube 12. As depicted, the surface 94 may include any suitable number of channels (e.g., channels 104 and 106) or bores to accommodate the camera 91 and any associated components, such as light sources. For example, in embodiments in which the camera 91 includes a plurality of fiber optic cables, the exterior surface 94 may include multiple channels. In other embodiments, the surface may include channels with a suitable size and shape to accommodate a CMOS chip and, in certain embodiments, a light source. In addition, the visualization device 18 may include features 100 that direct fluid to the surface of the optical components of the camera 91.

Portions of the visualization device 18 may be formed from the same material or different materials as the tube 12. Generally, the visualization device 18 may be formed from biocompatible polymers and other nonreactive materials. It should also be understood that certain portions of the visualization device may be coated with antimicrobial materials to prevent bacterial adhesion or fouling. In embodiments in which camera lenses are coated, the antimicrobial coatings may be selected to minimize interference with image acquisition. The visualization device 18 may be adhered to or fastened to the tube 12 by any suitable process. For example, the visualization device 18 may be embedded in or adhered (e.g., welded) to tubular body 12. In addition, the exterior portion 92 may provide an attachment surface that may be affixed to the distal tip 84. Coupling to the tube 12 may be assisted by threading cables or other attachments into a lumen. In particular embodiments, the tubular body 12 may include notches or recesses within the walls that accommodate the visualization device 18 and that do not impact the inner diameter of the ventilation lumens.

Figure 4:
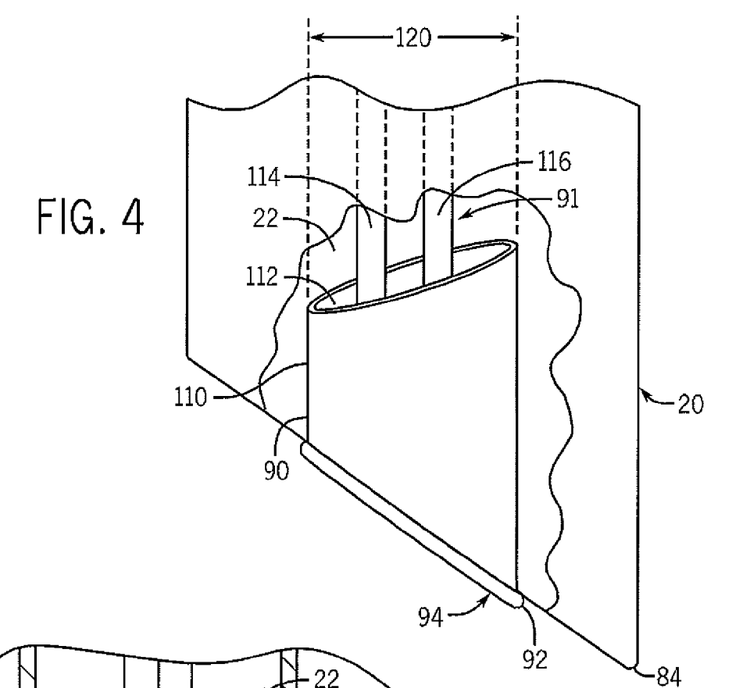
FIG. 4 is a partial cutaway view of the distal tip with an inserted visualization device holder of FIG. 2.

FIG. 4 is a side cutaway view of the visualization device 18. The holder 90 includes an interior or inserted portion 110 that is disposed within the suction lumen 22. The inserted portion 110 forms an annulus or partial annulus that defines a channel 112 accommodating, as depicted in this implementation, fibers 114, 116 that may be part of camera 91. As noted, the exterior portion 92 may be adhered to the distal tip 84. In addition, the inserted portion 110 may further affix the holder 90 via compression forces and adhesive.

Figure 5:
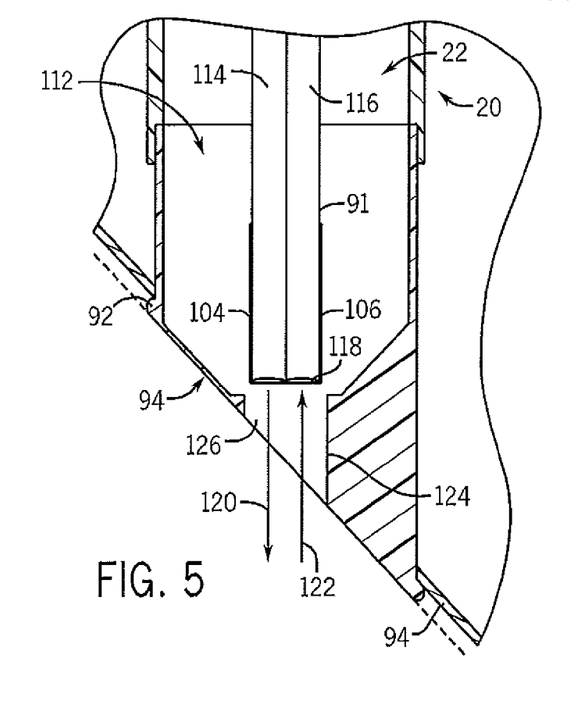
FIG. 5 is a sectional view of the distal tip with an inserted visualization device holder showing the camera angle relative to the angle of distal tip.

The holder 90 may dictate a particular alignment of the camera 91 with the tube 12, which in turn may define a field of view for the camera 91. As shown in cross-section in FIG. 5, the holder 90 may include an abutment surface 118 that may hold the camera components away from the exterior of the tube 12. The abutment surface 118 may at least in part define the field of view for the camera 91 by aligning the optical components of the camera with the tube 12. The abutment surface 118 may form openings that facilitate visualization or may include optically transparent materials. In addition, the channels 104, 106 may also influence the angle of visualization. As shown, the camera may emit light along arrow 120 and receive light along arrow 122. Depending on the angles of these arrows 120, 122, the field of view of the camera 91 may be altered. As shown the arrows 120, 122 are nonorthogonal with the plane 123 of the distal tip 84. In this manner, the holder 90 facilitates visualization in a distal direction, which may assist proper placement of the tube 12. Further, this field of view may be achieved without bulky or protruding alignment features that decrease the available ventilation diameter.

Figures 6, 7:
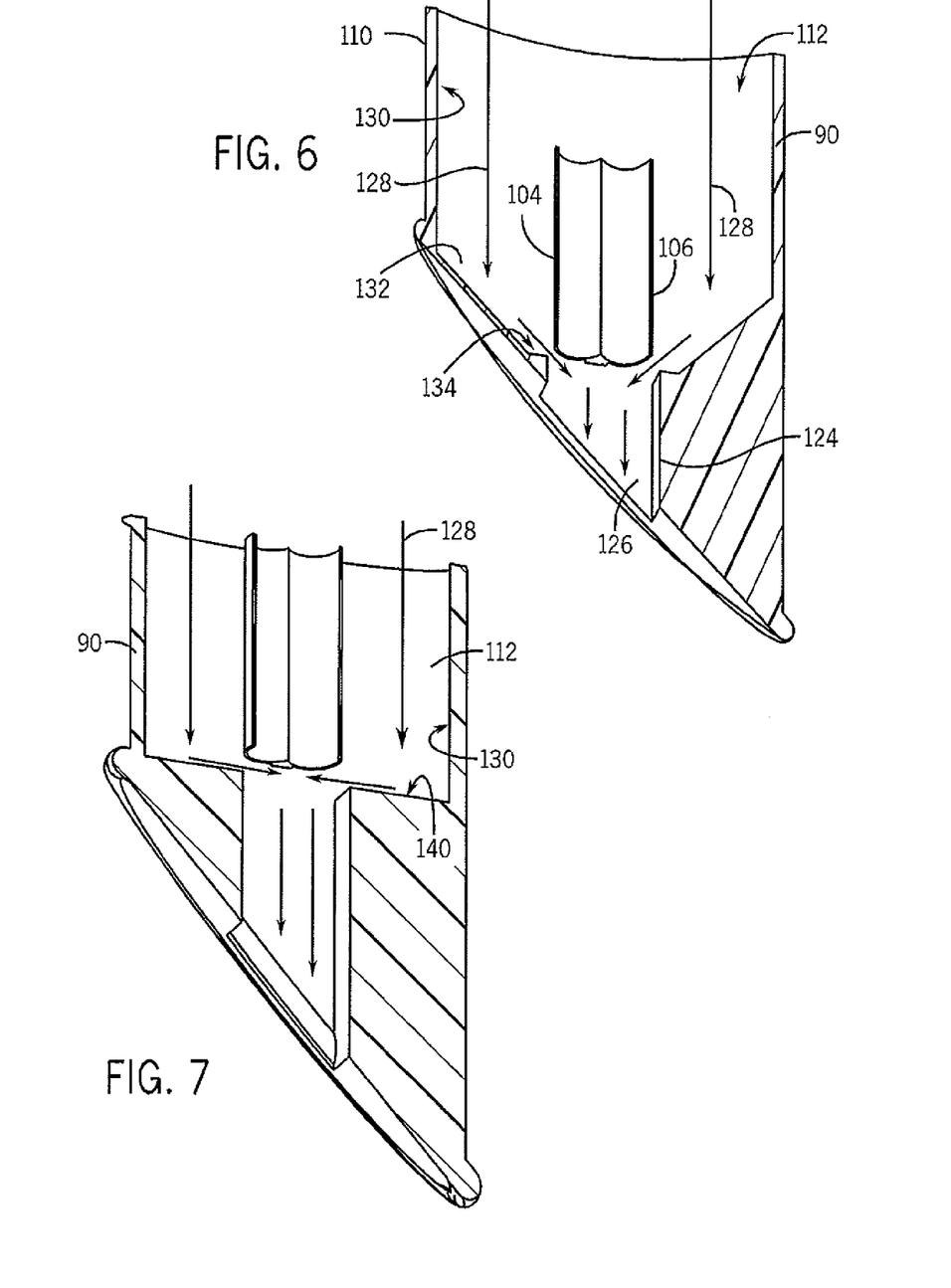
FIG. 6 is a sectional view of a visualization device holder including an air gap with air-directing surfacing that may be used in conjunction with a tracheal tube.
FIG. 7 is a sectional view of a visualization device holder in which the air-directing surfaces are flat.

The depicted configuration may also protect the camera from secretions. The camera 91 is recessed in the suction lumen 22 within a bore 124 in the exterior surface 94 defining a passageway 126, which may prevent direct buildup of secretions on surface of the camera 91. In addition, this configuration may facilitate cleaning and/or flushing of the camera surface. As shown in cross-section in FIG. 6, the holder 90 may include shaped surfaces that direct fluid flow, shown as arrows 128, around the channels 104 and 106 that hold the camera 91. The fluid may be delivered via a proximal connection of the lumen (e.g. lumen 22) with a fluid source. The fluid delivered via the lumen enters the holder 90 through the channel 112 and follows a path dictated by surrounding channel surface 130 to slanted surface 132 and notch 134. The fluid may exit the holder 90 and the tube 12 through passageway 126. The flow path of the fluid is directed towards the visualization surfaces of the camera 91 to clean any accumulated debris. In addition, the flushing may remove any mucus plugs or other secretions that may collect on the exterior surface 94 of the holder 90. In particular embodiments, the fluid may be a gas (e.g., a suitable respiratory gas) or a liquid (e.g., saline). The angles and shapes of the surfaces defining the fluid flow path may be altered depending on the orientation and shape of the camera 91. As shown in cross-section in FIG. 7, the holder 90 may define a flat surface 136 that may direct fluid with more force directly onto a camera surface.

Figure 8:
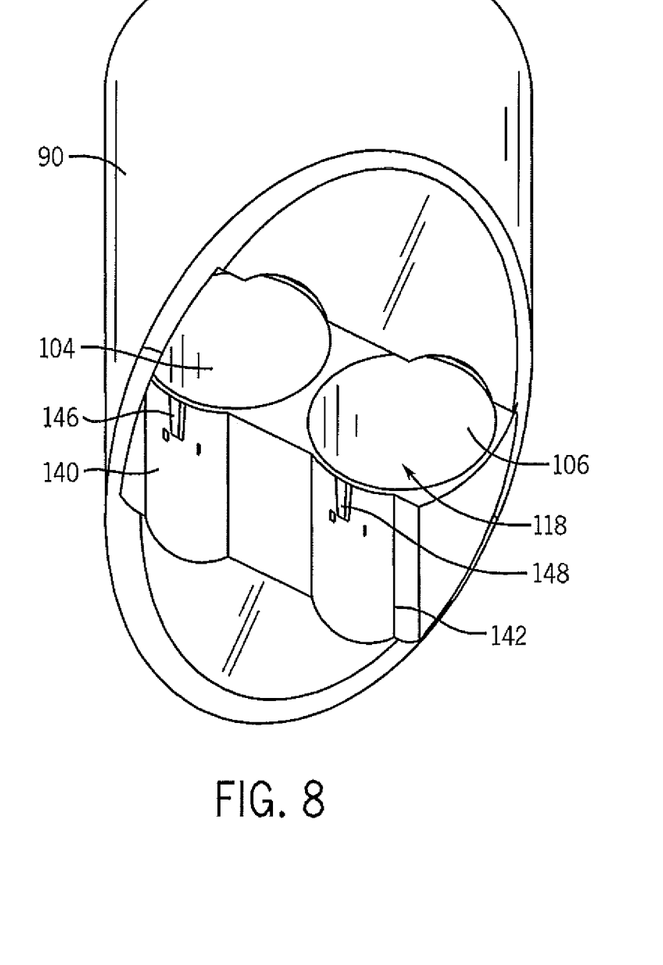
FIG. 8 is a perspective view of a visualization device holder including dedicated channels for fluid flow.

In other embodiments, the holder 90 may define dedicated passageways or channels for fluid flow. FIG. 8 is a perspective view of an exemplary holder 90 with fluid flow channels 140 and 142 that are located adjacent the camera channels 104, 106. Rather than allowing free flow of fluid within the interior negative space of the holder 90, the fluid flow channels 140 and 142 may define a strict path of fluid from the lumen to the camera 91. This configuration may involve lower volumes of flushing fluid, which may reduce any effects of flushing fluid on concentrations of respiratory gases.

The fluid flow channels 140 and 142 may include additional fluid directing features, such as notches 146 and 148, which may interrupt the flow downward through the channels 140 and 142 to induce a spray onto the camera 91. It should be understood that the fluid directing features may be of any suitable size, shape, and orientation to influence the fluid flow onto the camera 91. For example, a fluid directing feature may include a protrusion, a recess, or a notch. As shown, notches 146 and 148 are located distally from the abutment surface 118. In addition, fluid directing features may also facilitate exit of fluid from the holder 90, which may facilitate clearing mucus plugs from the exterior surface 94.

Figures 9, 10:
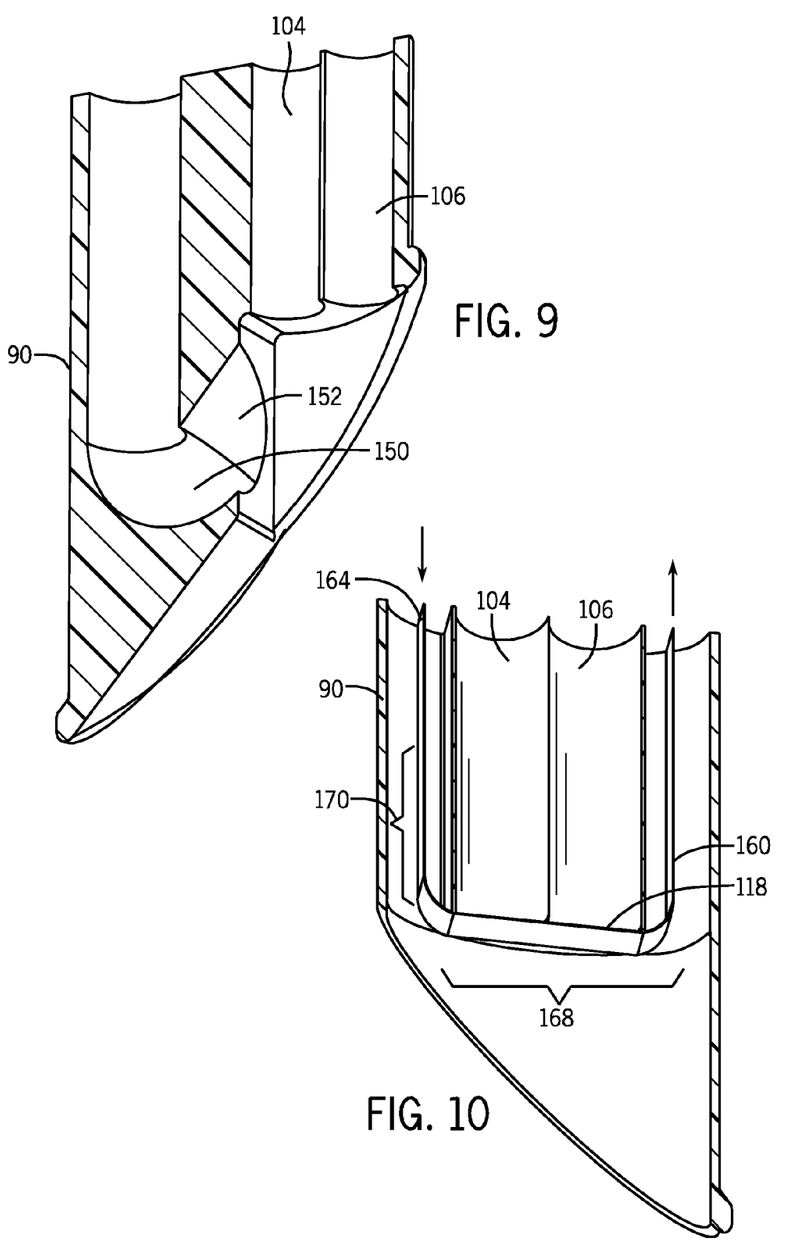
FIG. 9 is a sectional view of a visualization device holder for accommodating a fluid flush line in the lumen.
FIG. 10 is a sectional view of a visualization device holder including a movable cleaning member.

In an alternative embodiment, FIG. 9 is a sectional view in which the holder 90 may accommodate a dedicated flush line that may extend through a lumen (e.g., lumen 22). For example, a 3Fr Bespack valve, part 7406-02 (Bespack, Norfolk, UK), may be threaded into the lumen and may direct fluid through channel 150 onto the camera. In one implementation, the fluid flush line may be adhered to the holder 90 as a unitary assembly. In other embodiments, the holder 90 may be aligned with the fluid flush line (e.g., channel 150 may be aligned with the valve or the valve may be threaded into the channel 150) during manufacturing. The channel 150 may include angle portions, such as angled portion 152 to direct the fluid.

The holder 90 may also facilitate mechanical cleaning of the camera 91. FIG. 10 is a sectional view of a holder that includes a movable member 160. The movable member 160 may be a flexible tape or film that is positioned to loop around the bottom of the channels 104 and 106 to cover the abutment surface 118. The movable member may be optically transparent so that visualization through the holder 90 is substantially unaffected. As shown, the movable member 160 may include ends 164 and 166 that may extend proximally through the lumen. In one embodiment, the ends 164 and 166 exit the tube 12 at a proximal location and are accessible to a user or a mechanical control system. Displacement of the ends 164 and 166 at their proximal exit points results in the portion 168 moving relative to the camera 91. This mechanical motion of the movable member 160 moves an adjacent portion 170 onto the abutment surface 118. In this manner, cleaner portions of the movable member 160 may be exposed as other portions are covered with secretions. Further, the movable member acts as an additional protective surface for the camera 91.

Figure 11:
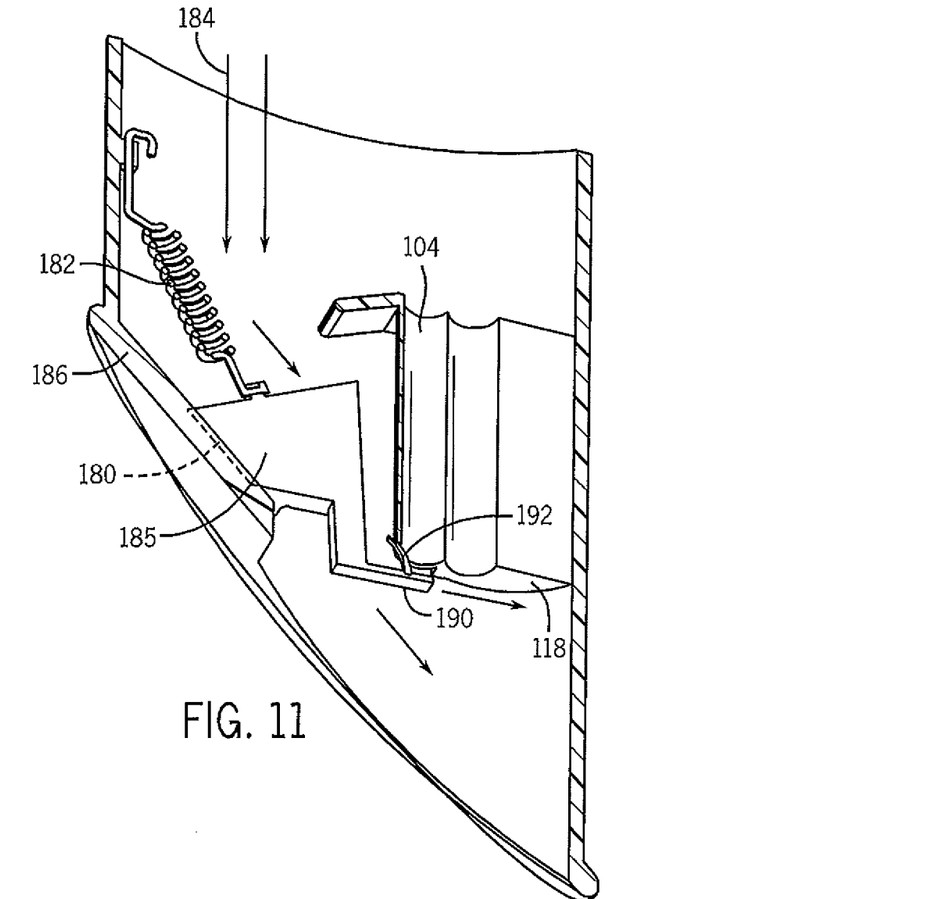
FIG. 11 is a sectional view of a visualization device holder including an air or fluid-triggered movable cleaning member.

FIG. 11 is a sectional view of a holder 90 that includes a fluid-triggered mechanical wiper assembly 180 in an undeployed state. The mechanical wiper member 180 is spring-loaded such that an application of force to the spring, e.g., via fluid flow along the path of arrows 184, moves the mechanical wiper member assembly 180 within the holder. As depicted, the mechanical wiper assembly 180 includes a body portion 185 that is configured to move along the slanted wall 186 of the holder 90. This in turn displaces the wiper member 190 along the abutment surface 118 in the direction of arrow 191. Cessation of fluid force allows the spring to return to its unbiased position. That is, in the absence of fluid flow, the wiper is positioned so that the viewing field of the camera 91 may be generally unobstructed. In certain embodiments, the wiping member 190 may include a spacer 192 configured to hold the wiper member 190 away from the camera in the undeployed state. The camera 91 is only obstructed during the deployed state, e.g., when fluid is applied.

While the disclosure may be susceptible to various modifications and alternative forms, specific embodiments have been shown by way of example in the drawings and have been described in detail herein. However, it should be understood that the embodiments provided herein are not intended to be limited to the particular forms disclosed. Rather, the various embodiments may cover all modifications, equivalents, and alternatives falling within the spirit and scope of the disclosure as defined by the following appended claims.

What is claimed is:

1. A tracheal tube, comprising:
    a ventilation lumen having a distal end and a proximal end and configured to transfer a fluid to a patient's lungs;
    a second lumen running along and integrally formed within an exterior wall of the ventilation lumen; and
    a visualization device disposed on a distal tip of the second lumen and comprising:
        a housing coupled to the distal tip having an exterior portion and an inserted portion, wherein the exterior portion terminates in a flange at the distal tip, and wherein the inserted portion is positioned at least in part within the distal tip of the second lumen and comprises a first channel, a second channel, and a third channel, wherein the first channel terminates in a passageway having a diameter that is smaller than a diameter of the first channel, wherein the second channel and the third channel are disposed within the first channel, and wherein the second and third channels terminate proximal to the exterior portion; and
        a camera coupled to the housing and disposed within the second channel, the third channel, or a combination thereof such that the camera is positioned at least in part within the second lumen.

2. The tracheal tube of claim 1, wherein the tracheal tube is configured to be coupled to at least one of a ventilator, a bag for ventilation, inspiration valving, expiration valving, or an air supply.

3. The tracheal tube of claim 1, wherein the second lumen extends the length of the ventilation lumen and forms a passageway to an exterior of the tracheal tube at a location proximal to an inflatable cuff.

4. The tracheal tube of claim 1, comprising a cuff inflation lumen that forms a passageway to an exterior of the tracheal tube at a location in fluid communication with an interior of an inflatable cuff.

5. The tracheal tube of claim 1, wherein the second lumen has an inner diameter of about 3 millimeters or less.

6. The tracheal tube of claim 1, wherein the camera comprises one or more fiber optic cables.

7. The tracheal tube of claim 6, wherein the one or more fiber optic cables are about 1 mm or less in diameter.

8. The tracheal tube of claim 1, wherein the second lumen is configured to deliver air or fluid to a surface of the camera.

9. The tracheal tube of claim 1, wherein the camera is recessed within the housing.

10. The tracheal tube of claim 9, wherein the housing comprises one or more surfaces configured to direct air or fluid onto a surface of the camera.

11. The tracheal tube of claim 1, wherein the housing comprises a moveable member configured to move relative to the camera.

12. The tracheal tube of claim 11, wherein the moveable member comprises a covering having an extending portion that extends through a proximal end of the second lumen, wherein manipulating the extending portion causes the covering to move relative to the camera.

13. The tracheal tube of claim 11, wherein the moveable member comprises a wiper configured to at least in part cover the camera in a deployed state, wherein the deployed state is triggered by applying a mechanical force within the second lumen.

14. The tracheal tube of claim 1, wherein the distal tip of the ventilation lumen is slanted and wherein an exterior portion of the housing conforms to the slant.

15. The tracheal tube of claim 1, wherein the second lumen comprises an evacuation lumen.

16. The tracheal tube of claim 1, wherein the housing comprises an abutment surface positioned at the distal end of the second and third lumens, and wherein the abutment surface at least in part defines a field of view of the camera.

17. A tracheal tube, comprising:
a ventilation lumen having a distal end and a proximal end and configured to transfer a fluid to a patient's lungs;
a second lumen running along and integrally formed within an exterior wall of the ventilation lumen such that the second lumen is fluidically isolated from the ventilation lumen; and
a visualization device affixed to the tracheal tube at a distal end of the second lumen and comprising:
a housing having an exterior portion and an inserted portion, wherein the inserted portion is positioned at least in part within the second lumen and comprises a first channel, a second channel, and a third channel, wherein the first channel terminates in a passageway having a diameter that is smaller than a diameter of the first channel, wherein the second channel and the third channel are disposed within the first channel, and wherein the second and the third channels terminate proximal to the exterior portion; and
a camera coupled to the housing and disposed within the second channel, the third channel, or a combination thereof, such that the camera is positioned at least in part within the second lumen, and wherein the housing holds the camera in a fixed position relative to the tracheal tube and wherein the fixed position defines a field of view for the camera that is generally oriented towards a carina when the tracheal tube is inserted into a patient.

18. The tracheal tube of claim 17, wherein the distal end of the ventilation lumen is slanted and wherein an exterior portion of the housing conforms to the slant.

19. The tracheal tube of claim 17, wherein the housing is coupled to the distal end of the second lumen.

20. The tracheal tube of claim 17, wherein the exterior portion comprises a flange extending away from the distal end of the second lumen.

* * * * *